United States Patent [19]

Hesch

[11] Patent Number: 5,127,039
[45] Date of Patent: Jun. 30, 1992

[54] SAMPLE HOLDER FOR X-RAY DIFFRACTOMETRY

[75] Inventor: Victor L. Hesch, Los Alamos, N. Mex.

[73] Assignee: The United States of America as represented by the United States Department of Energy, Washington, D.C.

[21] Appl. No.: 641,832

[22] Filed: Jan. 16, 1991

[51] Int. Cl.⁵ .................................. G01N 23/20
[52] U.S. Cl. ........................ 378/79; 378/71; 378/81; 378/73; 378/205; 378/208; 250/491.1
[58] Field of Search .................. 378/71, 70, 73, 79, 378/81, 205, 34, 35, 208; 250/491.1

[56] References Cited

U.S. PATENT DOCUMENTS

| | | | |
|---|---|---|---|
| 4,525,852 | 6/1985 | Rosenberg | 378/34 |
| 4,641,329 | 2/1987 | Green et al. | 378/79 |
| 4,771,446 | 9/1988 | Howe et al. | 378/73 |
| 4,788,702 | 11/1988 | Howe et al. | 378/71 |

Primary Examiner—Janice A. Howell
Assistant Examiner—Kim-Kwok Chu
Attorney, Agent, or Firm—Milton D. Wyrick; Paul D. Gaetjens; William R. Moser

[57] ABSTRACT

A sample holder for use with X-ray diffractometers with the capability to rotate the sample, as well as to adjust the position of the sample in the x, y, and z directions. Adjustment in the x direction is accomplished through loosening set screws, moving a platform, and retightening the set screws. Motion translators are used for adjustment in the y and z directions. An electric motor rotates the sample, and receives power from the diffractometer.

2 Claims, 4 Drawing Sheets

SAMPLE HOLDER FOR X-RAY DIFFRACTOMETRY

BACKGROUND OF THE INVENTION

The present invention relates to the field of X-ray diffractometry, and, more specifically, to mounts or holders for sample materials undergoing X-ray diffractometry. The invention is a result of a contract with the Department of Energy (Contract No. W-7405-ENG-36)

In the practice of X-ray diffractometry, it is important to mount the material to be investigated in a holder which allows the material to be axially adjusted with relation to the X-ray beam. One X-ray diffraction machine, which is in wide use in scientific research, is the model XDS 2000® manufactured by Scintag, Inc. of Santa Clara, Cal. This is the only X-ray diffractometer manufactured in the United States. Included as an accessary to this machine is a carousel known as a 4 sample spinner. It is well known that the ability to rotate samples is an important feature in the practice of X-ray diffractometry. However, the 4 sample spinner is designed to hold and spin loosely loaded powders. There is no mounting provided for the holding or spinning of solid materials.

The present invention provides a sample holder for X-ray diffractometry which may be used on the Scintag, Inc. diffractometer, and which is adaptable to any other X-ray diffractometers. It can provide three axis (x, y, and z axes) manual adjustment, and has a motor and a rotatable platform for rotating the sample.

It is an object of the present invention to provide apparatus which allows for an X-ray sample holder for use with X-ray diffractometers which allows 3-dimensional adjustment of the position of the sample.

It is another object of the invention to provide an X-ray sample holder which will rotate the sample.

It is a still further object of the invention to provide a sample holder which will contain both solid and powdered samples.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention provides a holder for solid materials to be investigated through X-ray diffractometry and comprises platform means for securing a sample to be investigated. Rotation means are rotatably connected to the platform means for rotating the platform. Axis adjustment means are in contact with the platform means for adjusting the platform means in a plurality of directions. Mounting means are connected to the platform means for mounting the platform means to a diffractometer.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
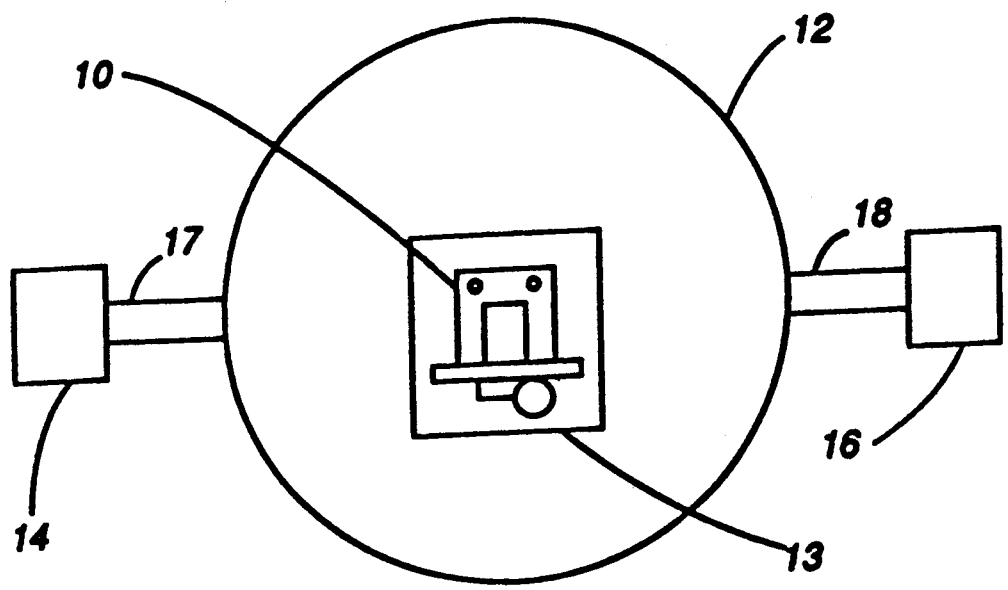
FIG. 1 is a schematic representation of the front of a diffractometer having a sample holder according to the present invention attached in position for analysis of a sample.

The present invention provides a sample holder for X-ray analysis of samples using a X-ray diffractometer such as is manufactured by Scintag, Inc. of Santa Clara, Cal. In FIG. 1, a multi-axis sample holder according to the present invention is schematically shown installed on X-ray diffractometer 12. In FIG. 1, sample holder 10 is mounted to front mounting plate 13 of the vertical $\theta-\theta$ goniometer of X-ray diffractometer 12 in a position to allow analysis of a sample by X-ray source 14 and X-ray detector 16.

In operation, after mounting sample holder 10 to diffractometer 12, a sample may be placed into holder 10, which can be positioned correctly in all three axes. After positioning, the sample can be irradiated by X-ray source 14, and the scattered X-rays collected by X-ray (scintillation) detector 16. Prior art sample holders have required the repositioning one or both of arm 17 and arm 18 to obtain a desired x, y position. However, no height, or z-axis, positioning was possible.

Figure 2:
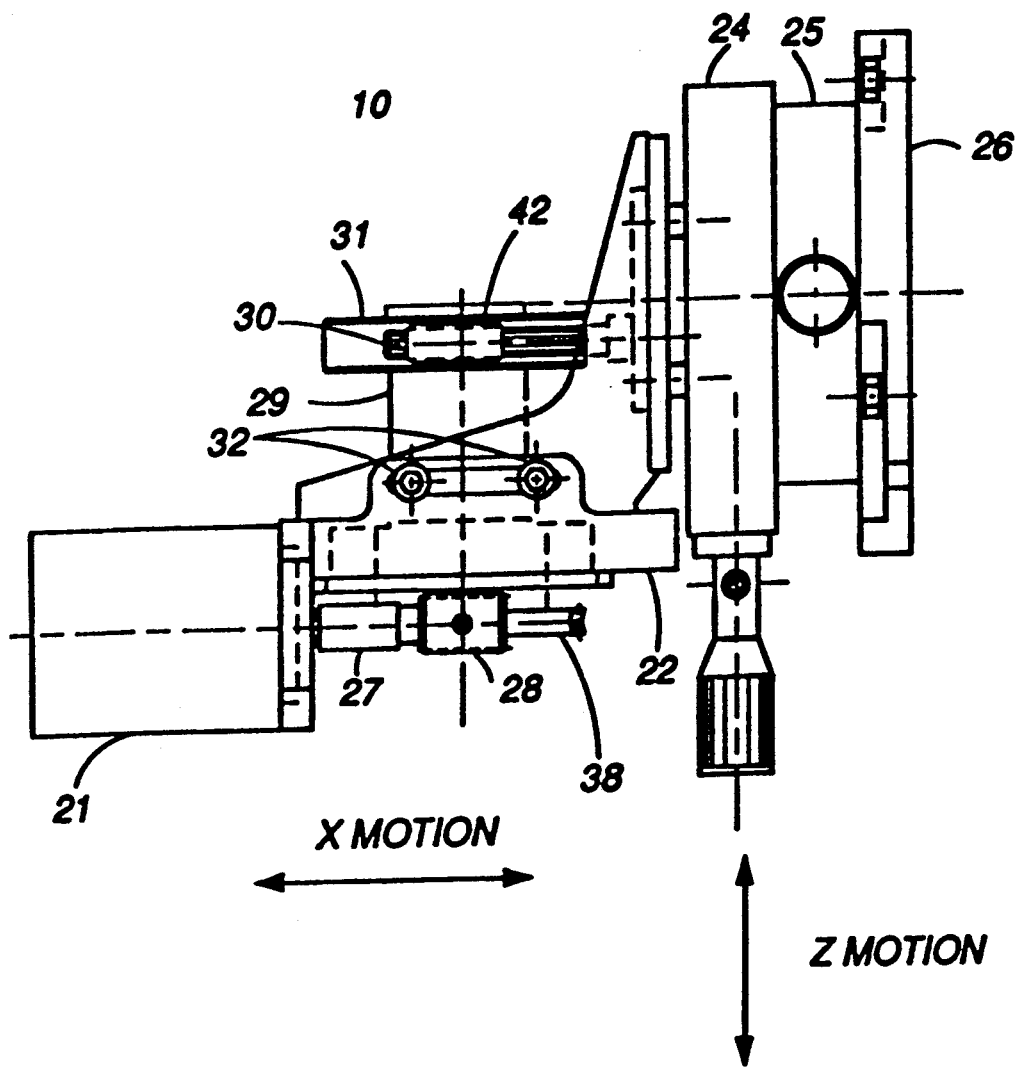
FIG. 2 is a side view of the sample holder according to the present invention.

Reference is now made to FIG. 2, where the components of holder 10 can be better seen and understood in this side view of the present invention. As seen, electric motor 21 is secured to X-axis platform 22, which is itself adjustably attached to Z motion translator 24, which in turn, attaches to Y motion translator 25. Finally, Y motion translator 25 is attached to mounting plate 26. It is mounting plate 26 which attaches sample holder 10 to an X-ray diffractometer 12 (FIG. 1) through mounting holes (not shown) located so as to mate with the particular mounting configuration of and X-ray diffractometer 12.

Motor 21 may be any electric motor which is suited for a particular application. In one embodiment, used with a Scintag, Inc. Model XDS 2000® X-ray diffractometer, motor 21 is capable of producing approximately 1800 rpm. A TRW Globe motor, model Number 75A120-2, may be used with good results in this embodiment. This motor is a 115 VAC, 60 Hz, 2 $\mu$F motor to match the requirements of the Scintag, Inc. diffractometer. Other motors would be used with other diffractometers, the only requirement being that the motor is compatible with the available power characteristics of the diffractometer.

Shaft coupling 27 of motor 21 is connected to worm 28, which is a conventional worm. For this embodiment, worm 28 and associated gear 38 has a reduction ratio of 30:1, and reduces the output rpm of the TRW Globe motor 21 to 60 rpm for sample cylinder 29. A Boston Gear worm, Model number GDTH may be employed as worm 28 in this embodiment. Worm 28 is rotatably coupled to sample cylinder 29. This may be accomplished by boring out the gear hub of gear 38 for a press fit with sample cylinder 29.

Cylinder 29 is, of course, the holder of the sample (not shown) which is to be irradiated by X-rays. Normally, the sample is placed into a sample disk (not shown) which is inserted into cylinder 29 from its bottom. The sample disks can be made to have a diameter slightly smaller than the inside diameter of cylinder 29, and can be configured to hold either a solid or powdered sample. The bottom of cylinder is thickened to have an outside diameter greater than the upper portion. This thickening of the bottom portion of cylinder 29 facilitates adaptation to bearing 46 (FIG. 3) and gear 38.

Motor 21, worm 28 and gear 38 can obviously be any of numerous models. It is only necessary to choose each according to the particular application, so that they each satisfy any special power supply or other requirements of the X-ray diffractometer on which the present invention is to be utilized.

Y motion translator 25 and Z motion translator 24 are conventional axis translators. One translator suitable for use as Y motion translator 25 and Z motion translator 24 is the Klinger model number MR 80.25. If adjustment is not desired in either the Y or Z directions, either of Y motion translator 25 or Z motion translator 24 can be omitted.

Dowels 30 are connected to inner bracket 23 (FIG. 3) and extend slidably through wings 42 of slide body 31. A plan view of slide body 31 is shown in FIG. 4 which more clearly shows its configuration. Slide body 31 encircles cylinder 29, and along with dowels 30, stabilizes cylinder 29 while allowing rotation of cylinder 29 and X-axis adjustment with X-axis platform 22. X-axis platform 22 is adjusted and fixed in position by loosening and retightening set screws 32, which are located on both sides of X-axis platform 22.

Figure 3:
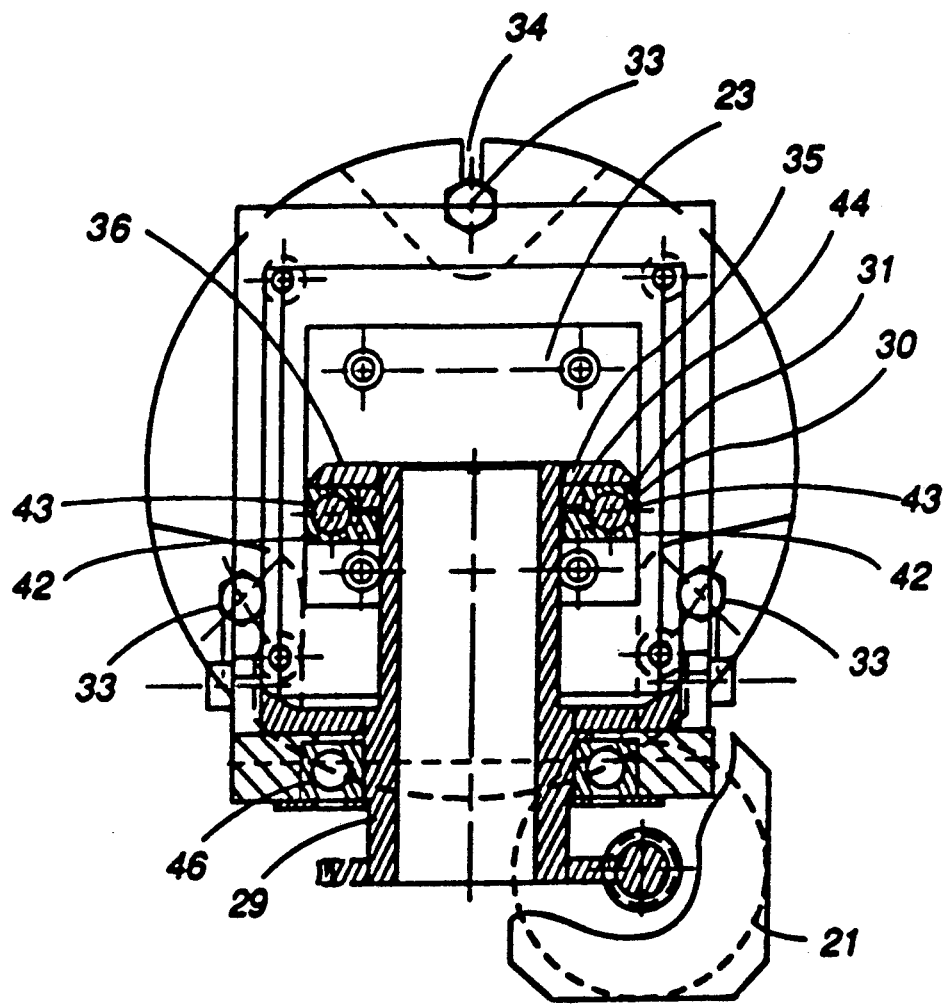
FIG. 3 is a cross-sectional front view of the sample holder according to the present invention.
Figure 4:
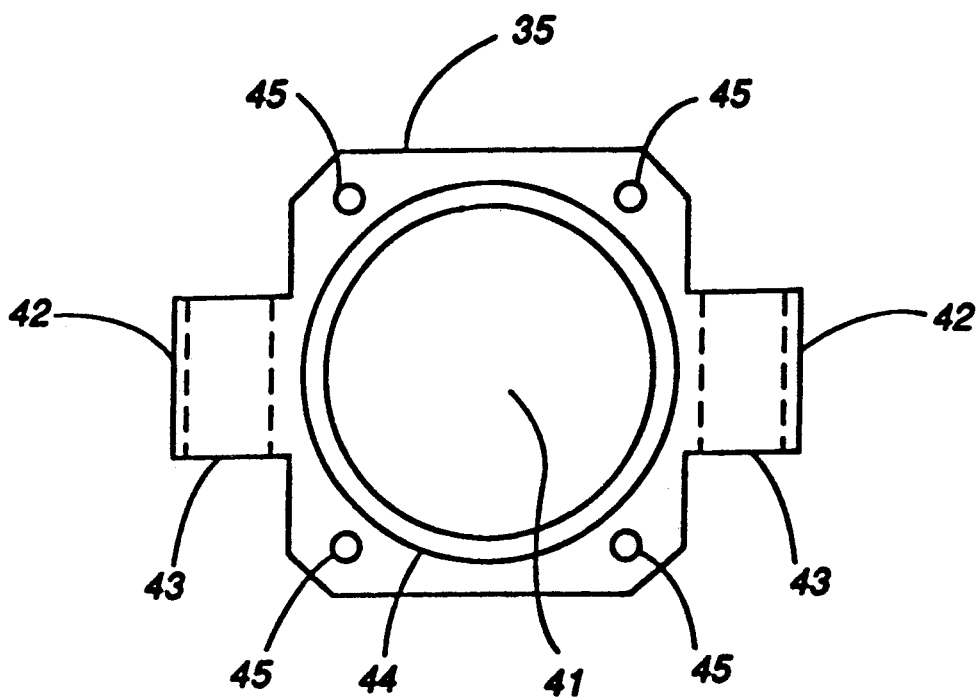
FIG. 4 is a plan view of the slide body component of the present invention.

The invention can be seen in a front view in FIG. 3. Here, the arrangement between dowels 30 and wings 42 of slide body 31 can be clearly seen. Also in this view, mounting bolts 33 are illustrated in place in slots 34. Slots 34 can be repositioned as required for mounting to various X-ray diffractometers.

Here, slide body 31 defines cylindrical channels 43 and radial recess 44. Cylindrical channels 43 slidably accommodate dowels 30, and radial recess 44 accepts Teflon ® ring which is in contact with cylinder 29 The thickened bottom portion of cylinder 29 is more easily seen in this figure. Ring cover plate 36 retains Teflon ® ring 35 in radial recess 44 and is attached to slide body 31. This combination of slide body 31, Teflon ® ring 35, and ring cover plate 36 serves to rotatably stabilize cylinder 29 as it is rotated by motor 21, worm 28 and gear 38 (FIG. 2).

For greater clarity, reference should be made to FIG. 4, wherein there is illustrated plan view of slide body 31 as it is configured for the embodiment of the invention shown in FIGS. 2 and 3. As seen, slide body 31 defines central aperture 41, which is axially located to accommodate cylinder 29 (FIG. 3). Slide body 31 also defines radial recess 44 about central aperture 41 for placement of Teflon ® ring 35. Teflon ® ring 35 is maintained in radial recess 44 by ring cover plate 36 (FIG. 3), which has substantially the same shape as slide body 31.

Slide body 31 also defines wings 42 having cylindrical channels 43 for slidably accepting dowels 30 (FIG. 3). This allows the X-axis adjustment of the present invention. The four tapped openings 45 accept mounting screws (not shown) for mounting ring cover plate 36.

The foregoing description of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An x-ray sample holder for an X-ray diffractometer having a vertical $\theta-\theta$ gonimeter comprising:
   platform means for securing a sample to be investigated;
   an electric motor having a rotation speed of approximately 1800 rpm coupled to a worm and gear having a reduction ratio of approximately 30:1 in contact with said platform for rotating said platform means;
   axis adjustment means in contact with said platform means for adjusting said platform in a plurality of directions; and
   mounting means connected to said platform means for mounting said platform means to said vertical $\theta-\theta$ gonimeter of said diffractometer;
   wherein said electric motor and said worm and gear rotate said platform means at a rate of 1 rotation per second.

2. An X-ray sample holder for an X-ray diffractometer having a vertical $\theta-\theta$ gonimeter comprising:
   platform means comprising a cylinder having a top portion with a first outside diameter and a bottom portion with a second outside diameter larger than said first outside diameter for securing a sample to be investigated;
   an electric motor having a rotation speed of approximately 1800 rpm coupled to a worm and gear having a reduction ratio of approximately 30:1 in contact with said platform for rotating said platform means;
   axis adjustment means in contact with said platform means for adjusting said platform means in a plurality of directions; and
   mounting means connected to said platform means for mounting said platform means to said vertical $\theta-\theta$ gonimeter of said diffractometer.

* * * * *